United States Patent
Govari et al.

(10) Patent No.: US 10,786,304 B2
(45) Date of Patent: Sep. 29, 2020

(54) TEMPERATURE MEASUREMENT IN CATHETER

(71) Applicant: BIOSENSE WEBSTER (ISRAEL) LTD., Yokneam (IL)

(72) Inventors: Assaf Govari, Haifa (IL); Christopher Thomas Beeckler, Brea, CA (US); Andres Claudio Altmann, Haifa (IL)

(73) Assignee: Biosense Webster (Israel) Ltd., Yokneam (IL)

(*) Notice: Subject to any disclaimer, the term of this patent is extended or adjusted under 35 U.S.C. 154(b) by 338 days.

(21) Appl. No.: 15/949,252

(22) Filed: Apr. 10, 2018

(65) Prior Publication Data
US 2018/0221088 A1    Aug. 9, 2018

Related U.S. Application Data

(62) Division of application No. 14/642,135, filed on Mar. 9, 2015, now Pat. No. 9,956,035.
(Continued)

(51) Int. Cl.
*A61B 18/12* (2006.01)
*A61B 18/14* (2006.01)
(Continued)

(52) U.S. Cl.
CPC ...... *A61B 18/1492* (2013.01); *A61B 18/1206* (2013.01); *A61B 2017/003* (2013.01);
(Continued)

(58) Field of Classification Search
CPC ............ A61B 18/1492; A61B 18/1233; A61B 2018/0022; A61B 2018/00214;
(Continued)

(56) References Cited

U.S. PATENT DOCUMENTS 6,226,542 B1    5/2001    Reisfeld
6,301,496 B1    10/2001   Reisfeld
(Continued)

FOREIGN PATENT DOCUMENTS

CN    102106752 A    6/2011
CN    103156683 A    6/2013
(Continued)

OTHER PUBLICATIONS

Price, M.D., Adam et al., "Novel Ablation Catheter Technology that Improves Mapping Resolution and Monitoring of Lesion Maturation", The Journal of Innovations in Cardiac Rhythm Management, Jan. 2012, pp. 599-609, 3.
(Continued)

*Primary Examiner* — Thomas A Giuliani

(57) ABSTRACT

Ablation of cardiac tissue is carried out by inserting a probe having an ablation electrode and a plurality of microelectrodes into a body of a living subject to establish contact between two of the microelectrodes and target tissue, and energizing the ablation electrode. While the ablation electrode is energized impedances are measured between the microelectrodes, and the power level of the ablation electrode adjusted according to the impedances.

9 Claims, 6 Drawing Sheets

Related U.S. Application Data

(60) Provisional application No. 61/971,135, filed on Mar. 27, 2014.

(51) Int. Cl.
 *A61B 18/00* (2006.01)
 *A61B 34/20* (2016.01)
 *A61B 17/00* (2006.01)

(52) U.S. Cl.
 CPC ............... *A61B 2018/0022* (2013.01); *A61B 2018/00351* (2013.01); *A61B 2018/00577* (2013.01); *A61B 2018/00642* (2013.01); *A61B 2018/00702* (2013.01); *A61B 2018/00803* (2013.01); *A61B 2018/00875* (2013.01); *A61B 2018/1405* (2013.01); *A61B 2034/2051* (2016.02)

(58) Field of Classification Search
 CPC .. A61B 2018/00351; A61B 2018/0016; A61B 2018/162; A61B 2018/165; A61B 2018/1467; A61B 2018/1497; A61B 2018/00636; A61B 2018/00642; A61B 2018/00648; A61B 2018/00357; A61B 2018/00702; A61B 2018/00708; A61B 2018/00791; A61B 2018/00875; A61B 2018/00577
 USPC ........ 606/34, 35, 38, 41, 42, 49, 50; 607/98, 607/99, 102, 104, 105, 113, 115, 116, 607/122
 See application file for complete search history.

(56) References Cited

U.S. PATENT DOCUMENTS

| | | | |
|---|---|---|---|
| 6,332,089 | B1 | 12/2001 | Acker et al. |
| 6,618,612 | B1 | 9/2003 | Acker et al. |
| 6,690,963 | B2 | 2/2004 | Ben-Haim et al. |
| 6,814,733 | B2 | 11/2004 | Yitzhack Schwartz et al. |
| 6,892,091 | B1 | 5/2005 | Ben-Haim et al. |
| 6,997,924 | B2 | 2/2006 | Schwartz et al. |
| 7,156,816 | B2 | 1/2007 | Schwartz et al. |
| 7,536,218 | B2 | 5/2009 | Govari et al. |
| 8,414,579 | B2 | 4/2013 | Kim et al. |
| 8,668,686 | B2 | 3/2014 | Govari et al. |
| 9,687,289 | B2 | 6/2017 | Govari et al. |
| 2004/0068178 | A1 | 4/2004 | Govari |
| 2004/0102769 | A1 | 5/2004 | Schwartz et al. |
| 2004/0147920 | A1 | 7/2004 | Keidar |
| 2007/0156128 | A1* | 7/2007 | Jimenez ............ A61B 18/1206 606/34 |
| 2008/0243214 | A1 | 10/2008 | Koblish |
| 2009/0187187 | A1 | 7/2009 | Asirvatham et al. |
| 2009/0275827 | A1* | 11/2009 | Aiken ................ A61B 5/063 600/424 |
| 2010/0168548 | A1 | 7/2010 | Govari et al. |
| 2011/0106075 | A1 | 5/2011 | Jimenez |
| 2012/0116386 | A1 | 5/2012 | Govari et al. |
| 2012/0143177 | A1* | 6/2012 | Avitall ............... A61B 18/1492 606/21 |
| 2012/0157890 | A1 | 6/2012 | Govari et al. |
| 2013/0123778 | A1 | 5/2013 | Richardson et al. |
| 2013/0158545 | A1 | 6/2013 | Govari et al. |
| 2013/0178910 | A1* | 7/2013 | Azamian ............. A61B 18/06 607/33 |
| 2014/0058375 | A1 | 2/2014 | Koblish |
| 2014/0266235 | A1* | 9/2014 | Mathur .................. G01R 31/50 324/509 |
| 2016/0175041 | A1 | 6/2016 | Govari et al. |

FOREIGN PATENT DOCUMENTS

| | | |
|---|---|---|
| CN | 103190951 A | 7/2013 |
| EP | 1 803 410 A1 | 7/2007 |
| WO | WO 96/00036 A1 | 1/1996 |
| WO | WO 2008/118992 A1 | 10/2008 |
| WO | WO 2013/052590 A1 | 4/2013 |

OTHER PUBLICATIONS

European Search Report dated Sep. 29, 2015 in corresponding European Patent Application No. 15160978.1.

Chinese First Office Action dated Aug. 1, 2018 from corresponding Chinese Patent Application No. 201510141377.3.

\* cited by examiner

TO IMPEDANCE
MEASURING CIRCUITRY

TEMPERATURE MEASUREMENT IN CATHETER

CROSS-REFERENCE TO RELATED APPLICATIONS

The present application is a divisional of U.S. patent application Ser. No. 14/642,135, filed Mar. 9, 2015, now U.S. Pat. No. 9,956,035, which claims priority to U.S. Provisional Patent Application Ser. No. 61/971,135, filed on Mar. 27, 2014, the entirety of these applications being incorporated herein by reference thereto.

BACKGROUND OF THE INVENTION

1. Field of the Invention

This invention relates to invasive medical devices. More particularly, this invention relates to ablation of tissue using such devices.

2. Description of the Related Art

Ablation of body tissue using electrical energy is known in the art. The ablation is typically performed by applying alternating currents, for example radiofrequency energy, to the electrodes, at a sufficient power to destroy target tissue. Typically, the electrodes are mounted on the distal tip of a catheter, which is inserted into a subject. The distal tip may be tracked in a number of different ways known in the art, for example by measuring magnetic fields generated at the distal tip by coils external to the subject.

A known difficulty in the use of radiofrequency energy for cardiac tissue ablation is controlling local heating of tissue. There are tradeoffs between the desire to create a sufficiently large lesion to effectively ablate an abnormal tissue focus, or block an aberrant conduction pattern, and the undesirable effects of excessive local heating. If the radiofrequency device creates too small a lesion, then the medical procedure could be less effective, or could require too much time. On the other hand, if tissues are heated excessively then there could be local charring effects, coagulum, and or steam pops due to overheating. Such overheated areas can develop high impedance, and may form a functional barrier to the passage of heat. The use of slower heating provides better control of the ablation, but unduly prolongs the procedure.

Self-regulating tissue ablators have been proposed to achieve the desired control. For example, PCT International Publication WO9600036 discusses ablation of body tissue in which ablating energy is conveyed individually to multiple emitters in a sequence of power pulses. The temperature of each emitter is periodically sensed and compared to a desired temperature established for all emitters to generate a signal individually for each emitter based upon the comparison. The power pulse to each emitter is individually varied, based upon the signal for that emitter to maintain the temperatures of all emitters essentially at the desired temperature during tissue ablation.

Commonly assigned U.S. Patent Application Publication No. 2012/0157890, which is herein incorporated by reference, discloses performing tissue ablation out by determining a measured temperature of the tissue and a measured power level of transmitted energy to a probe, and controlling the power output level responsively to a function of the measured temperature and the measured power level.

SUMMARY OF THE INVENTION

According to disclosed embodiments of the invention, temperature is measured according to the changes in impedance between a pair of irrigated electrodes on a catheter. The usual temperature sensor found on such catheters can be omitted.

There is provided according to embodiments of the invention a method of ablation, which is carried out by inserting a probe having an ablation electrode and a plurality of microelectrodes into a body of a living subject. The method is further carried out by establishing a contacting relationship between two of the microelectrodes and a target tissue, and energizing the ablation electrode. While the ablation electrode is energized the method is further carried out by measuring an impedance between the two microelectrodes, and responsively to the impedance adjusting the power level of the ablation electrode.

A further aspect of the method includes iteratively measuring the impedance, and estimating a tissue temperature from a change between two measurements of the impedance.

Yet another aspect of the method includes making a determination that the tissue temperature exceeds a predetermined limit, and responsively to the determination reducing the power of the ablation electrode. The power may be reduced to zero to deactivate the ablation electrode.

According to still another aspect of the method, measuring an impedance is performed by polling the microelectrodes to determine pairwise impedances therebetween. The pair of the selected microelectrodes may have the highest and the second highest measured impedance.

According to a further aspect of the method, measuring an impedance includes measuring a bipolar impedance between the selected pair of the microelectrodes.

According to an additional aspect of the method, establishing a contacting relationship includes determining a location and orientation of the tip of the probe with respect to the target tissue with six degrees of freedom.

According to another aspect of the method, measuring an impedance includes polling the microelectrodes to determine impedances between the microelectrodes and an indifferent electrode.

One aspect of the method includes deploying an inflatable balloon through a lumen of the probe, wherein the microelectrodes are disposed circumferentially about the longitudinal axis of the balloon on its exterior wall.

Another aspect of the method the balloon includes a subassembly comprising a plurality of strips extending longitudinally on the exterior wall of the balloon, and the microelectrodes are disposed on the strips.

There is further provided according to embodiments of the invention an apparatus for carrying out the above-described method.

BRIEF DESCRIPTION OF THE SEVERAL VIEWS OF THE DRAWINGS

For a better understanding of the present invention, reference is made to the detailed description of the invention, by way of example, which is to be read in conjunction with the following drawings, wherein like elements are given like reference numerals, and wherein.

DETAILED DESCRIPTION OF THE INVENTION

In the following description, numerous specific details are set forth in order to provide a thorough understanding of the various principles of the present invention. It will be apparent to one skilled in the art, however, that not all these details are necessarily needed for practicing the present invention. In this instance, well-known circuits, control logic, and the details of computer program instructions for conventional algorithms and processes have not been shown in detail in order not to obscure the general concepts unnecessarily.

Figure 1:
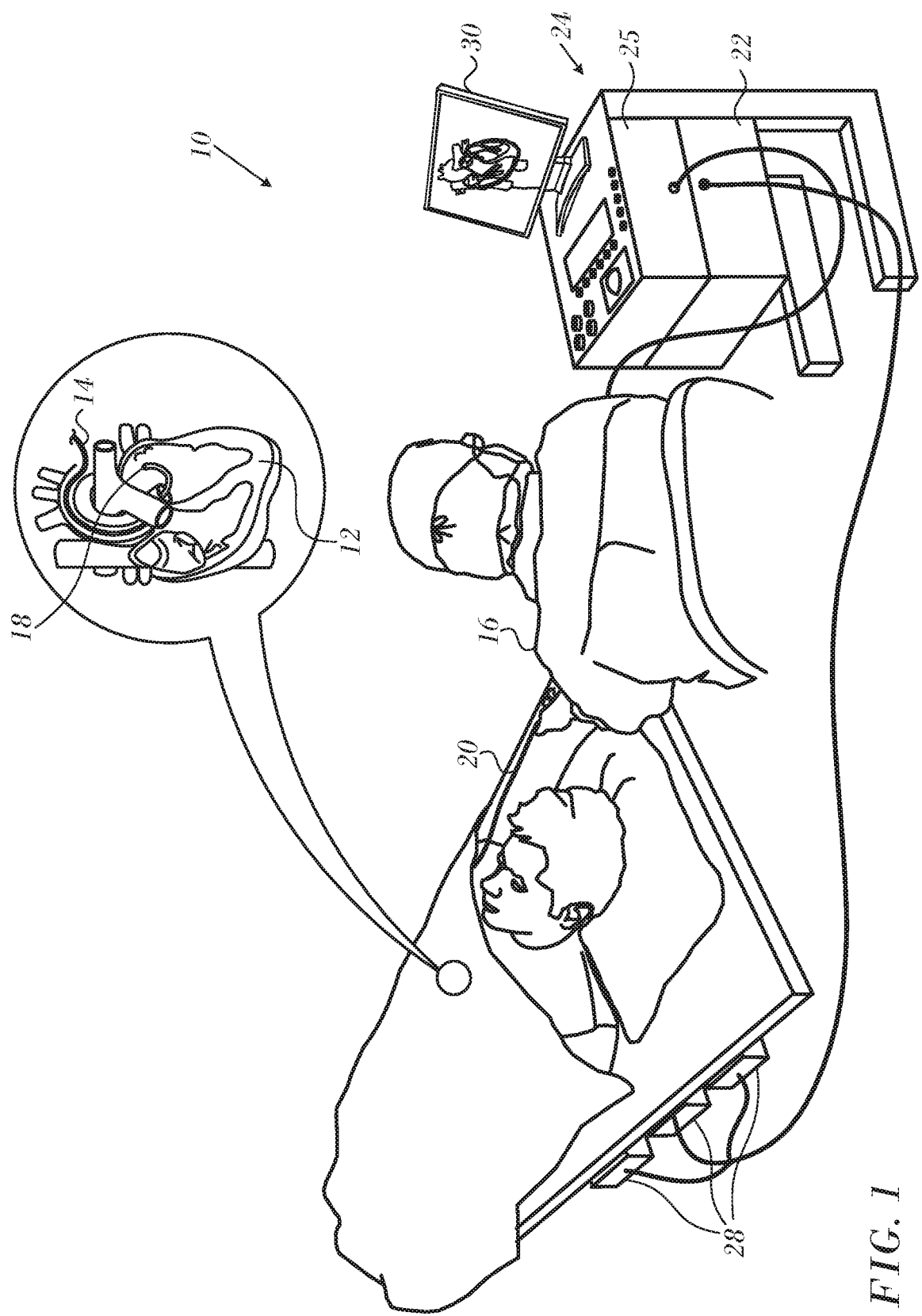
FIG. 1 is a pictorial illustration of a system for performing ablative procedures, which is constructed and operative in accordance with a disclosed embodiment of the invention.

Turning now to the drawings, reference is initially made to FIG. 1, which is a pictorial illustration of a system 10 for performing ablative procedures on a heart 12 of a living subject, which is constructed and operative in accordance with a disclosed embodiment of the invention. The system comprises a catheter 14, which is percutaneously inserted by an operator 16 through the patient's vascular system into a chamber or vascular structure of the heart. The operator 16, who is typically a physician, brings the catheter's distal tip 18 into contact with the heart wall at an ablation target site. Electrical activation maps may then be prepared, according to the methods disclosed in U.S. Pat. Nos. 6,226,542, and 6,301,496, and in commonly assigned U.S. Pat. No. 6,892,091, whose disclosures are herein incorporated by reference. Although the embodiment described with respect to FIG. 1 is concerned primarily with cardiac ablation, the principles of the invention may be applied, mutatis mutandis, to other catheters and probes and to body tissues other than the heart.

Areas determined to be abnormal by evaluation of the electrical activation maps can be ablated by application of thermal energy, e.g., by passage of radiofrequency electrical current through wires in the catheter to one or more electrodes at the distal tip 18, which apply the radiofrequency energy to the myocardium. The energy is absorbed in the tissue, heating it to a point (typically above 60° C.) at which it permanently loses its electrical excitability. When successful, this procedure creates non-conducting lesions in the cardiac tissue, which disrupt the abnormal electrical pathway causing the arrhythmia. Alternatively, other known methods of applying ablative energy can be used, e.g., ultrasound energy, as disclosed in U.S. Patent Application Publication No. 2004/0102769, whose disclosure is herein incorporated by reference. The principles of the invention can be applied to different heart chambers, when many different cardiac arrhythmias are present.

The catheter 14 typically comprises a handle 20, having suitable controls on the handle to enable the operator 16 to steer, position and orient the distal end of the catheter as desired for the ablation. To aid the operator 16, the distal portion of the catheter 14 contains position sensors (not shown) that provide signals to a positioning processor 22, located in a console 24. The console 24 typically contains an ablation power generator 25. The catheter 14 may be adapted to conduct ablative energy to the heart using any known ablation technique, e.g., radiofrequency energy, ultrasound energy, and laser energy. Such methods are disclosed in commonly assigned U.S. Pat. Nos. 6,814,733, 6,997,924, and 7,156,816, which are herein incorporated by reference.

The positioning processor 22 is an element of a positioning subsystem of the system 10 that measures location and orientation coordinates of the catheter 14.

In one embodiment, the positioning sub-system comprises a magnetic position tracking arrangement that determines the position and orientation of the catheter 14 by generating magnetic fields in a predefined working volume and sensing these fields at the catheter. The magnetic position tracking arrangement typically comprises a set of external radiators, such as field generating coils 28, which are located in fixed, known positions external to the patient. The field generating coils 28 are driven by field generators (not shown), which are typically located in the console 24, and generate fields, typically electromagnetic fields, in the vicinity of the heart 12.

In an alternative embodiment, a radiator in the catheter 14, such as a coil, generates electromagnetic fields, which are received by sensors (not shown) outside the patient's body.

Some position tracking techniques that may be used for this purpose are described, for example, in the above-noted U.S. Pat. No. 6,690,963, and in commonly assigned U.S. Pat. Nos. 6,618,612 and 6,332,089, and U.S. Patent Application Publications 2004/0147920, and 2004/0068178, whose disclosures are all incorporated herein by reference. Although the positioning sub-system shown in FIG. 1 uses magnetic fields, the methods described below may be implemented using any other suitable positioning system, such as systems based on electromagnetic fields, acoustic or ultrasonic measurements.

As noted above, the catheter 14 is coupled to the console 24, which enables the operator 16 to observe and regulate the functions of the catheter 14. Console 24 includes a processor, preferably a computer with appropriate signal processing circuits. The processor is coupled to drive a monitor 30. The signal processing circuits typically receive, amplify, filter and digitize signals from the catheter 14, including signals generated by the above-noted sensors and a plurality of sensing electrodes (not shown) located distally in the catheter 14. The digitized signals are received and used by the console 24 to compute the position and orientation of the catheter 14 and to analyze the electrical signals from the electrodes. The information derived from this analysis may be used to generate an electrophysiological map of at least a portion of the heart 12 or structures such as the pulmonary venous ostia, for diagnostic purposes such as locating an arrhythmogenic area in the heart or to facilitate therapeutic ablation.

Typically, the system 10 includes other elements, which are not shown in FIG. 1 for the sake of simplicity. For example, the system 10 may include an electrocardiogram (ECG) monitor, coupled to receive signals from one or more body surface electrodes, to provide an ECG synchronization signal to the console 24. The system 10 typically also includes a reference position sensor, either on an externally-applied reference patch attached to the exterior of the subject's body, or on an internally-placed catheter, which is inserted into the heart 12 maintained in a fixed position relative to the heart 12. Conventional pumps and lines for circulating liquids through the catheter 14 for cooling the ablation site are provided.

One system that embodies the above-described features of the system 10 is the CARTO® 3 System, available from Biosense Webster, Inc., 33 Technology Drive, Irvine, Calif. 92618. This system may be modified by those skilled in the art to embody the principles of the invention described herein.

Figure 2:
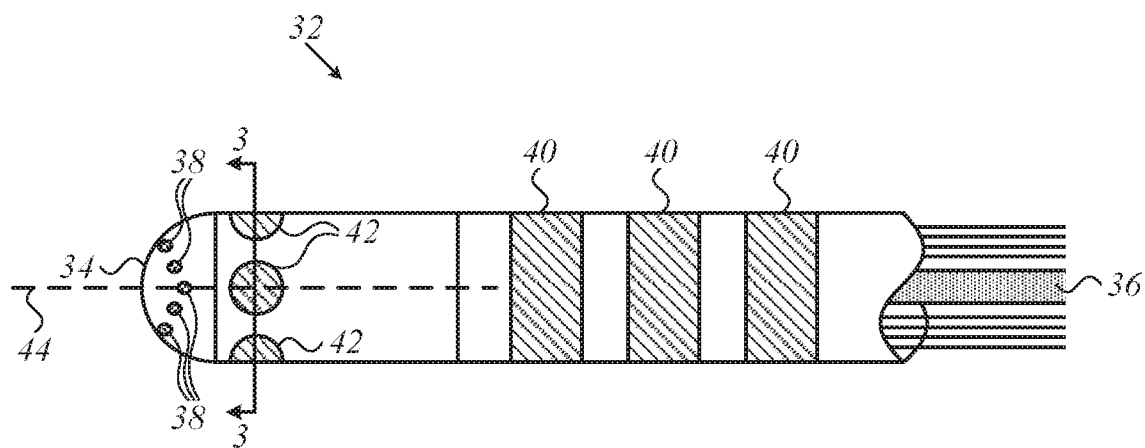
FIG. 2 is a schematic diagram of a distal portion of a catheter, in accordance with an embodiment of the invention.

Reference is now made to FIG. 2, which is a schematic diagram of a distal portion of a catheter 32, in accordance with an embodiment of the invention, which is suitable for use in the system 10 (FIG. 1). An ablation electrode 34 is disposed at the tip of the catheter 32. A hydraulic line 36 supplies irrigation fluid to cool an ablation site when the ablation electrode 34 is active. Pores 38 provide egress for the irrigation fluid. While the pores 38 may be placed through the ablation electrode 34, this is not essential, so long as the irrigation fluid exiting the pores 38 is able to bathe the ablation site. Mapping electrodes 40 may be provided for purpose of conventional electrophysiological mapping.

A series of microelectrodes 42 are positioned distally on the external surface of the catheter 32, They are disposed circumferentially its longitudinal axis 44 and close to the ablation electrode 34 such that at least two of the microelectrodes 42 and the ablation electrode 34 can be concurrently in firm contact with the target tissue when ablation is carried out. The inventors have found that measurements of bipolar impedance between the two contacting microelectrodes 42 is useful in determining the temperature of the target tissue.

One way of identifying a pair of contacting microelectrodes 42 is to determine their pairwise impedances, e.g., by polling. Either or both the magnitude and the phase of the impedance can be used. An additional way, due to the microelectrodes' small size, is to measure the impedance between a microelectrode and a back patch (indifferent electrode) to identify contact. Alternatively, the identification of a contacting pair of microelectrodes 42 can be achieved by exploiting the ability of a position tracking system (FIG. 1) such as the aforementioned CARTO system to determine the position and orientation of the catheter 32 with six degrees of freedom. Contact between a particular pair of the microelectrodes 42 can be determined by reference to the location and orientation of the tip of the catheter with respect to the target tissue.

Figure 3:
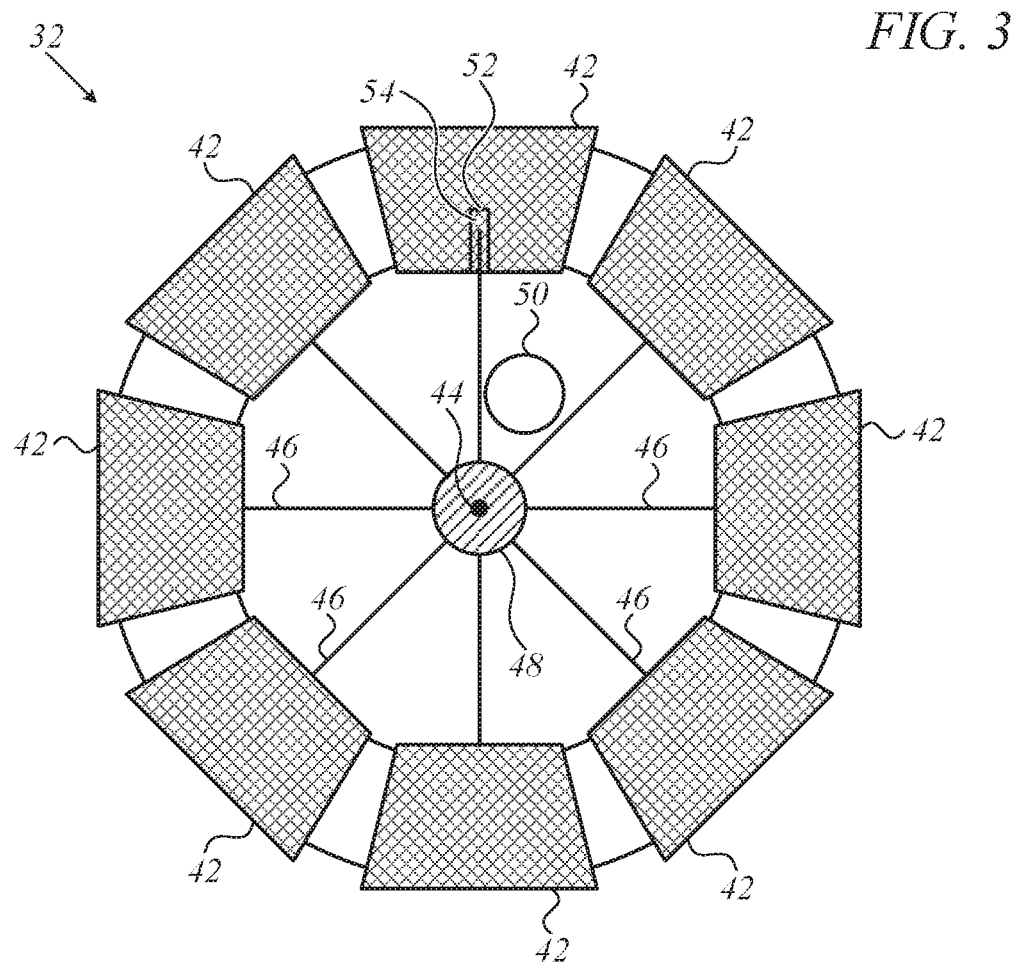
FIG. 3 is a sectional view through line 3-3 of FIG. 2, in accordance with an embodiment of the invention.

Reference is now made to FIG. 3, which is a sectional view through line 3-3 of FIG. 2, in accordance with an embodiment of the invention. The microelectrodes 42 are distributed generally evenly in perforations distributed about the circumference of the catheter 32. They microelectrodes 42 may be bonded within the perforations by suitable glues or bonding material. A flat profile of the outer surface exposed to the tissue is shown in this example. However, the profile of the microelectrodes 42 may be convex or sinusoidal. The profile of the microelectrodes 42 may be level with or raised above the external surface of the catheter 32. Wires 46 electrically connect the microelectrodes 42 to impedance measuring circuitry (not shown) via a cable 48. Hydraulic conduit 50 conducts irrigation fluid to the pores 38 (FIG. 1).

The microelectrodes 42 are composed of an electrically conductive material, such as platinum, palladium, gold, stainless steel, silver or silver chloride, all of which tend to maximize the coupling between the microelectrodes and the target tissue. The microelectrodes 42 are substantially solid, but may include a bore 52 that can receive and assure electrical connection between the wires 46 and the microelectrodes 42. The wires 46 may be secured to the microelectrodes 42 e.g., by solder 54, glue, or other convenient methods. Further details of the manufacture of the microelectrodes 42 are shown in U.S. Patent Application Publication No. 2014/0058375 and U.S. Pat. No. 8,414,579, the disclosures of which are herein incorporated by reference.

The microelectrodes 42 are dimensioned such that a desired number of them can be accommodated about the circumference of the catheter 32. The diameter of the microelectrodes 42 should be no greater than half the length of the ablation electrode 34, preferably no greater than one-fourth the length of the ablation electrode 34. The microelectrodes 42 should be spaced apart from one another by no more than one-half the diameter of the microelectrodes 42 (or one-half the shortest dimension in the case of non-circular embodiments).

Figure 4:
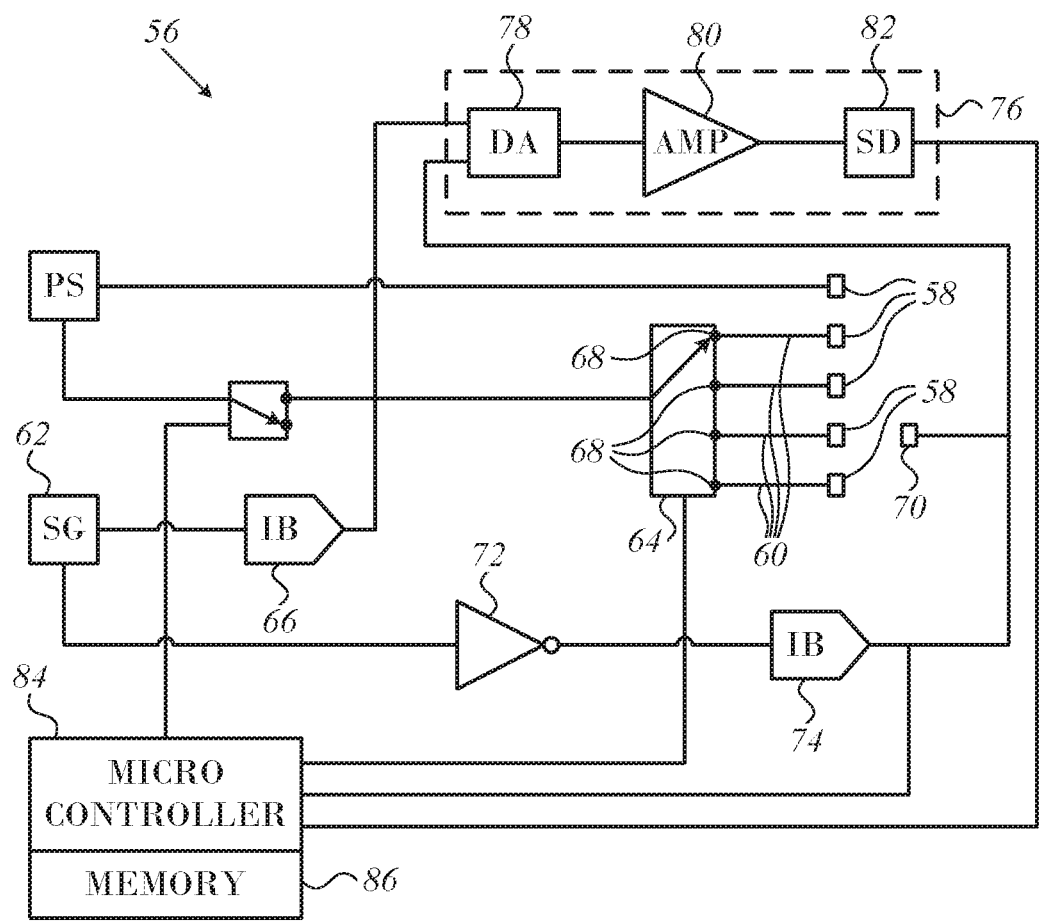
FIG. 4 is an electrical schematic of circuitry for impedance measurement during ablation, in accordance with an embodiment of the invention.

Reference is now made to FIG. 4, which is an electrical schematic of circuitry 56 for impedance measurement during ablation for temperature determination, in accordance with an embodiment of the invention. Multiple microelectrodes 58 are connected by respective lead wires 60 via the catheter handle (not shown). A signal generator 62 (SG) sends a high frequency test signal, e.g., an alternating current (AC) signal at about 2 μamps, in the frequency range of about 10 kHz to about 100 kHz, preferably about 50 kHz, to a multiplexer 64 via a high output impedance buffer 66 (IB).

The multiplexer 64 has multiple channels 68, each of which is in communication one of the microelectrodes 58, which receive the same current.

A return electrode 70 is also driven by the signal generator 102. The signal to the return electrode 70 is first inverted in phase by an inverter 72 and conditioned by high output impedance buffer 74.

Impedance measurement circuitry 76 (IMC) measures the impedance of each of the microelectrodes 58 as an indicator of the extent of its respective tissue contact and the condition of the tissue being ablated. The impedance measurement circuitry 76 includes a differential amplifier 78 (DA), an amplifier 80 (AMP) and a synchronous detector 82 (SD). The differential amplifier 78 measures a difference signal, specifically the voltage across a selected microelectrode 58 and the return electrode 70. The difference signal is further amplified by the amplifier 80 whose output is sent to the synchronous detector 82, which transforms the AC signal into a direct current (DC) signal and decreases the sensitivity of the circuitry 56 to external noise. The signal from the synchronous detector 82 is then used by a microcontroller 84 to control the multiplexer 64. To that end, the microcontroller 84 continuously stores in a memory 86 a plurality of different impedance signals from the synchronous detector 82 that equals the plurality of channels 68 in the multiplexer 64 (which is at least the plurality of microelectrodes 58 on the catheter), along with identification information on the channels 68 associated with each impedance value stored.

As such, the microcontroller 84 is at any time capable of identifying the channels 68 (and hence the microelectrodes 58) exhibiting the highest impedance value, which should be the microelectrode with the greatest tissue contact. Further details of the circuitry 56 are found in commonly assigned U.S. Patent Application Publication No. 2011/0106075, which is herein incorporated by reference.

Appropriate bipolar impedances between two microelectrodes can then be measured. This may be done by selecting the microelectrodes with the highest and second highest impedance, and providing signals from the microcontroller 84 to configure one of the two microelectrodes as the return electrode 70.

First Alternate Embodiment

Figure 5:
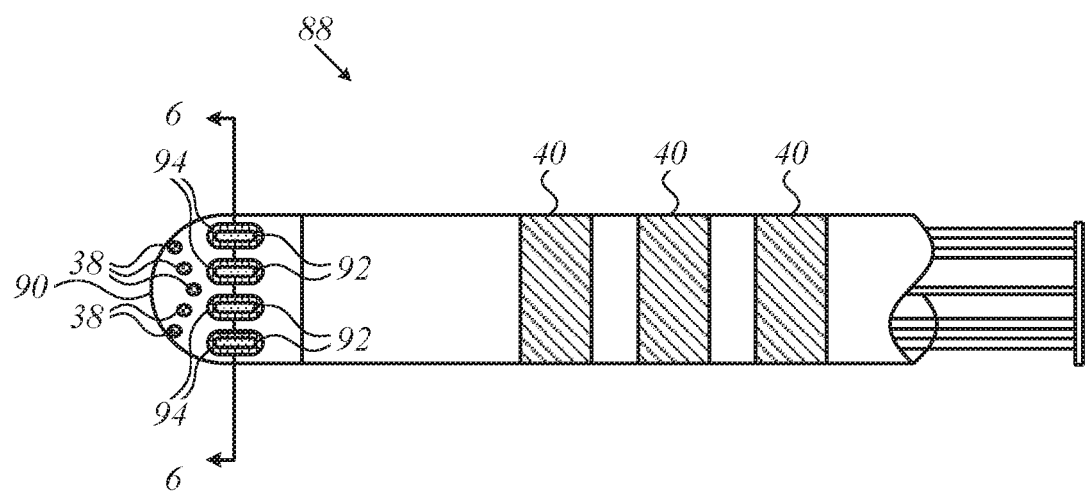
FIG. 5 is a schematic diagram of a distal portion of a catheter, in accordance with an embodiment of the invention'

Reference is now made to FIG. 5, which is a schematic diagram of a distal portion of a catheter 88, in accordance with an embodiment of the invention. Mounted on an ablation electrode 90 is a series of microelectrodes 92. The microelectrodes 92 are elongated in the longitudinal direction of the catheter 88, which allows a larger number to be accommodated than is the case with round microelectrodes having the same surface area. The elongated configuration is not essential, and, other configurations of the microelectrodes may be used. The microelectrodes 92 are thermally and electrically isolated from the ablation electrode 90 by an insulation layer 94.

Figure 6:
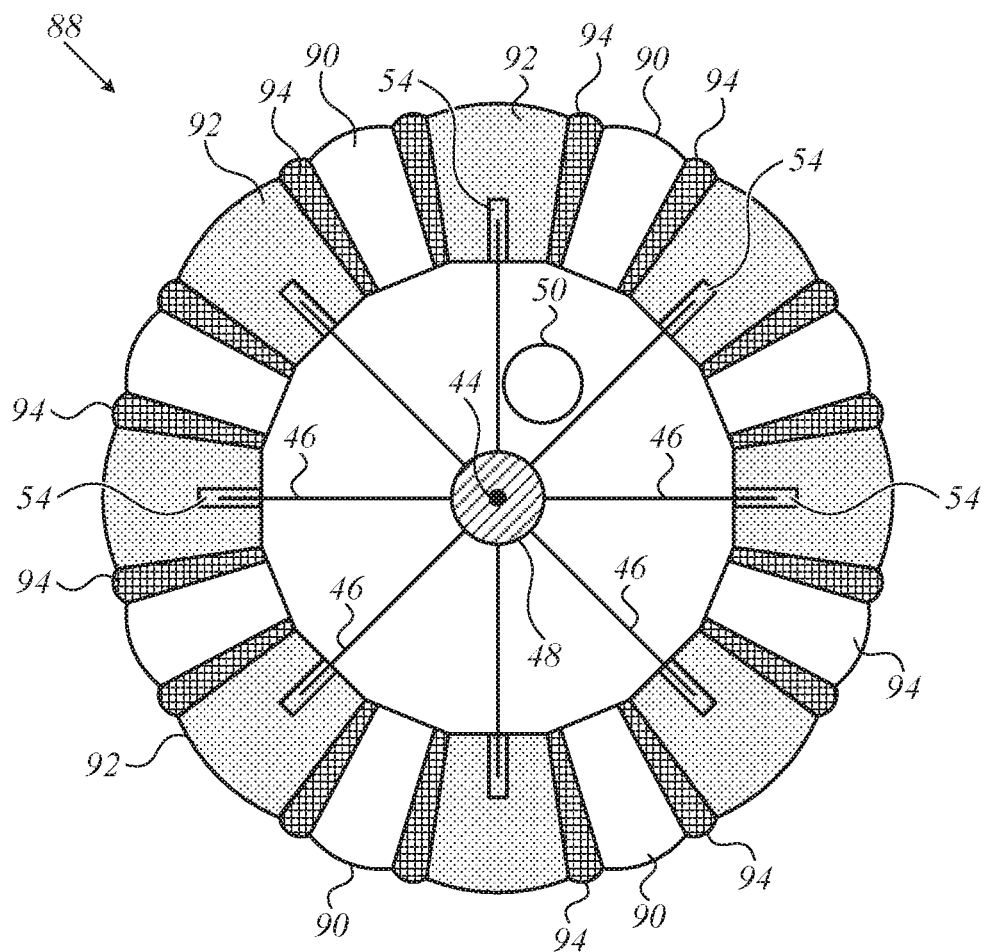
FIG. 6 is a sectional view through line 6-6 of FIG. 5, in accordance with an embodiment of the invention.

Reference is now made to FIG. 6, which is a sectional view through line 6-6 of FIG. 5, in accordance with an embodiment of the invention. The microelectrodes 92 are disposed within perforations through the ablation electrode 90. The insulation layer 94 surrounds the microelectrodes 92 and separates the microelectrodes 92 from the ablation electrode 90. As described in the above-noted U.S. Patent Application Publication No. 2014/0058375, the insulation layer 94 may be composed of the suitable electrically and thermally insulative material, such as a high temperature thermoset plastic with high dielectric properties, e.g., polyimide or plastics from the phenolic group, such as Bakelite® or Ultem® plastics. The insulation layer 94 and microelectrodes 92 may be bonded within the perforations using a suitable bonding material, such as epoxy.

Second Alternate Embodiment

Figure 7:
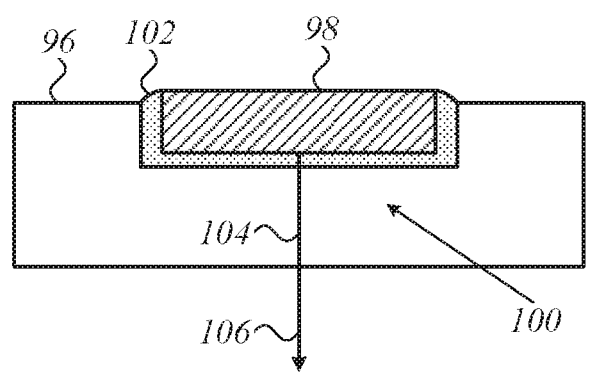
FIG. 7 is a schematic sectional view of a portion of an ablation electrode, in accordance with an embodiment of the invention.

This embodiment is similar to the embodiments of FIGS. 5 and 6, except that it is unnecessary to place large perforations in ablation electrode. Reference is now made to FIG. 7, which is a schematic sectional view of a portion of an ablation electrode 96, in accordance with an embodiment of the invention. A microelectrode 98 is embedded in a recess 100 formed in the wall of the ablation electrode 96 and separated from the ablation electrode 96 by a thermally and electrically insulative layer 102. A relatively small perforation 104 extending from the base of the recess 100 through the wall of the ablation electrode 96 carries a wire 106 into the interior of the catheter to ultimately connect to impedance measuring circuitry (not shown).

Third Alternate Embodiment

In this embodiment electrodes of a lasso, or loop, catheter having capabilities for ablation may be configured for bipolar impedance measurement. Such a catheter is known, for example from commonly assigned U.S. Patent Application Publication No. 2010/0168548, which is hereby incorporated by reference. Electrodes in contact with the tissue may be determined as described above.

Fourth Alternate Embodiment

Figure 8:
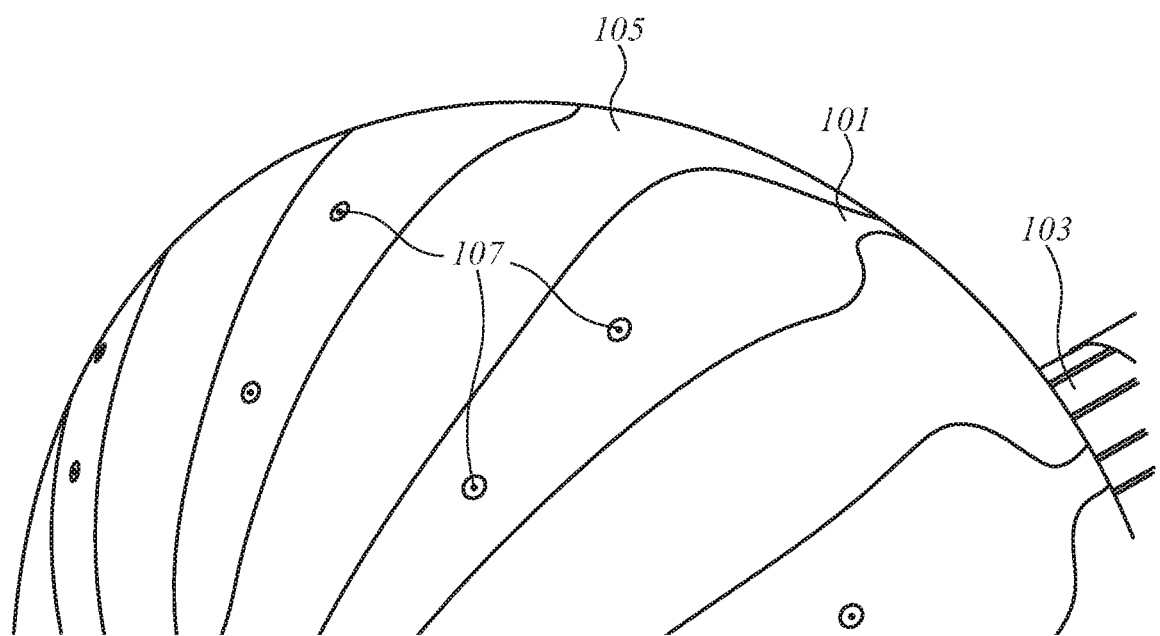
FIG. 8 is a pictorial view of a balloon assembly for a cardiac catheter in accordance with an alternate embodiment of the invention.

In this embodiment the microelectrodes are disposed on a flexible circuit substrate and adhered to the exterior of a balloon that can be inserted through a catheter and applied to the target as described in copending application Ser. No. 14/578,807, entitled Balloon for Ablation around Pulmonary Veins, which is herein incorporated by reference. Reference is now made to FIG. 8, which is a pictorial view of a balloon assembly for a cardiac catheter in accordance with an alternate embodiment of the invention. A subassembly, e.g., a flexible circuit board 101 is configured as multiple strips or bands radiating from shaft 103, extending longitudinally and adhering to the exterior wall of balloon 105 Arrays of microelectrodes 107 are disposed on the circuit board 101.

Operation.

Figure 9:
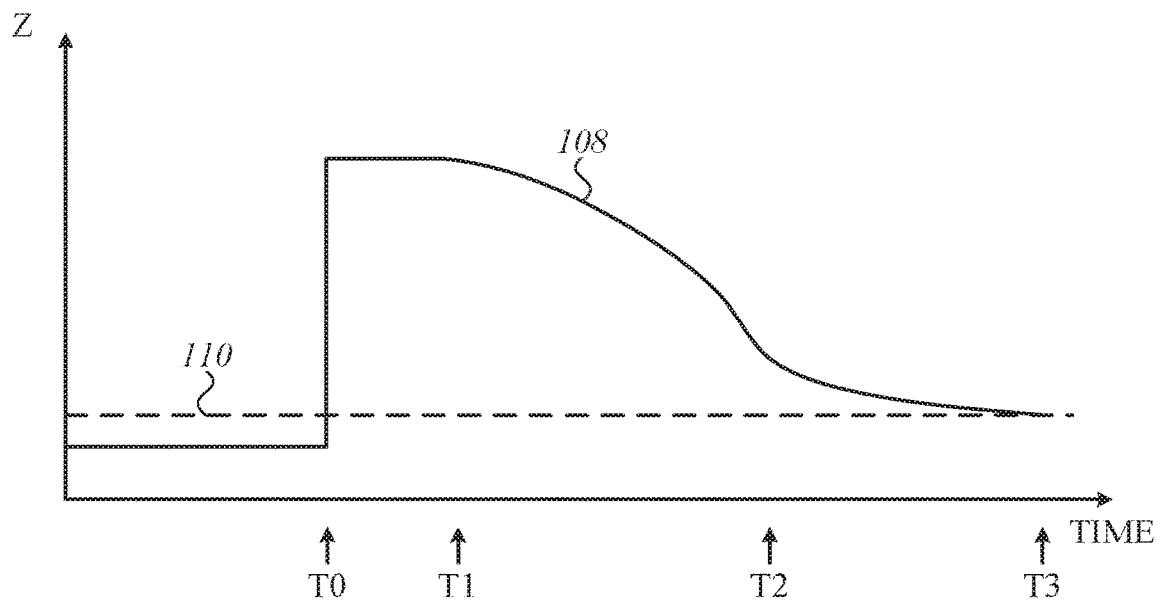
FIG. 9 is a tracing of bipolar impedance measured between two microelectrodes of a catheter, in accordance with an embodiment of the invention.

Reference is now made to FIG. 9, which is a prospective example of a tracing 108 that indicates bipolar impedance measured between two microelectrodes of a catheter during an ablation procedure, in accordance with an embodiment of the invention. Prior to time T0 the microelectrodes are out of contact with tissue, as evidenced by a relatively low impedance. At time T0, the electrodes have come into tissue contact, and the bipolar impedance rises. At time T1, the ablator is energized. Tissue temperature rises during the interval between times T1, T2, as evidenced by gradually decreasing bipolar impedance. At time T2, the ablator power is reduced, as the impedance is approaching a threshold indicated by broken line 110. Nevertheless, during the time interval T2-T3, impedance continues to decrease, albeit at a slower rate than prior to time T2. At time T3, the threshold of line 110 has been reached, and the ablator is deactivated. Actual impedance values vary according to the surface area of the microelectrodes, and are typically in the order of several hundred Ohms.

Figure 10:
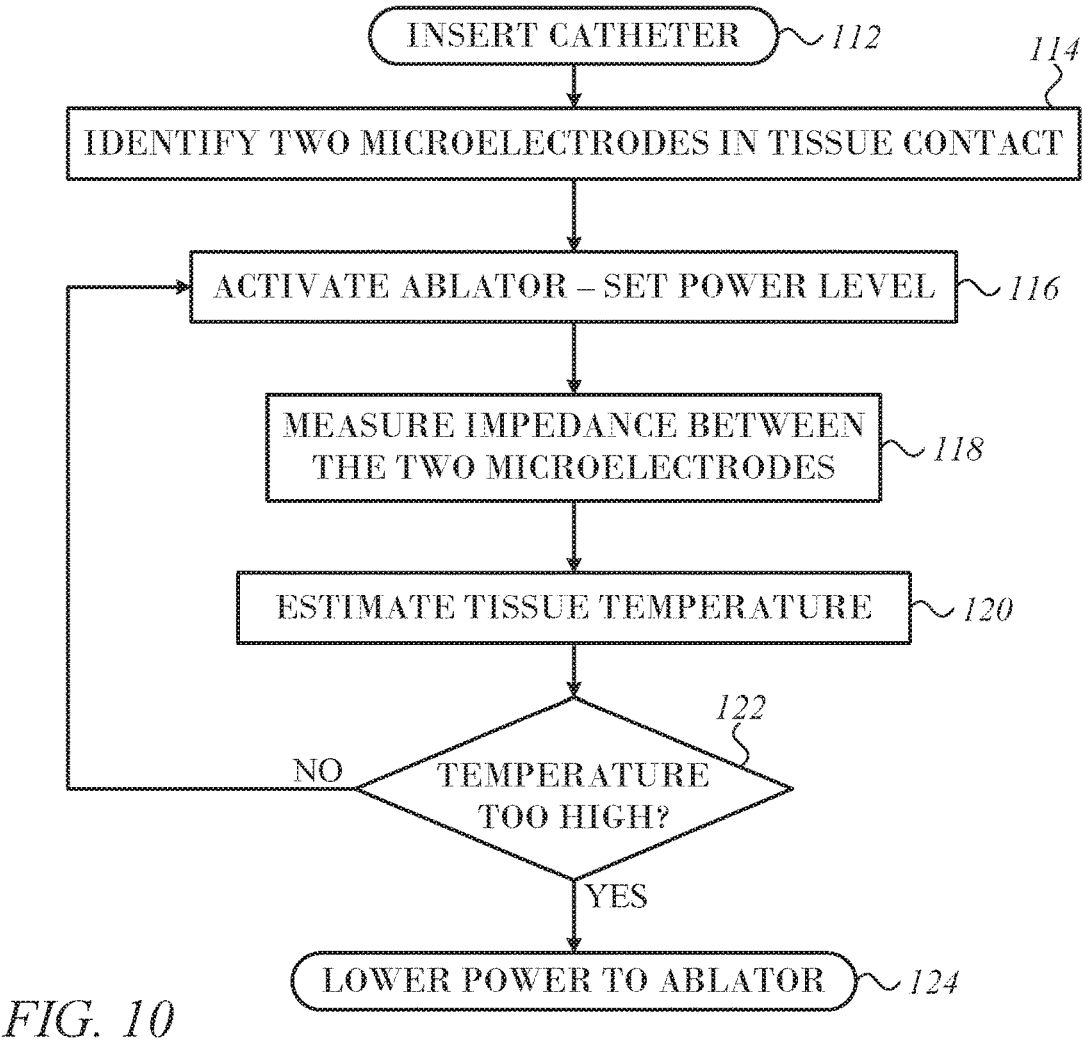
FIG. 10 is a flow chart of a method of tissue temperature determination during a catheterization procedure, in accordance with an embodiment of the invention.

Reference is now made to FIG. 10, which is a flow-chart of a method of tissue temperature determination during a catheterization procedure, in accordance with an embodiment of the invention. At initial step 112, a catheter in accordance with any of the above embodiments is inserted into contact with target tissue of a subject. The target is typically the endocardial surface of a heart chamber.

Next, at step 114 two microelectrodes of the catheter are determined to be in contact with the target. This determination may be made, for example, using the position processor of the CARTO system as noted above, by polling the microelectrodes pairwise until an impedance level consistent with tissue contact is identified, or measuring the impedance between a microelectrode and a backpatch (indifferent electrode), or a combination of the above.

Next, at step 116 the ablator is energized and its power level set. Irrigation fluid is caused to flow onto the ablation electrode and the target tissue.

Next, at step 118, while the ablator is active, bipolar impedance measurements are taken between the pair of electrodes identified in step 114.

Next, at step 120, tissue temperature is estimated based on the change in the impedance measurements, either absolute or as a percentage, and using, for example, empirical data from simulations that reveals a correlation similar to the plot in FIG. 9.

Next, at decision step 122, it is determined if the temperature is too high for continued ablation. If the determination at decision step 122 is negative, then control returns to step 116.

If the determination at decision step 122 is affirmative then control proceeds to final step 124, where the power level of the ablator is lowered. The power level of the ablator may be adjusted manually or automatically by a controller in accordance with known algorithms, for example as taught in commonly assigned U.S. Patent Application Publication No. 2012/0157890, which is herein incorporated by reference. The process iterates until the time set for the ablation expires, at which the power to the ablator is reduced or the ablator deactivated entirely by reducing the power to zero.

It will be appreciated by persons skilled in the art that the present invention is not limited to what has been particularly shown and described hereinabove. Rather, the scope of the present invention includes both combinations and sub-combinations of the various features described hereinabove, as well as variations and modifications thereof that are not in the prior art, which would occur to persons skilled in the art upon reading the foregoing description.

The invention claimed is:

1. A method of ablation, comprising the steps of: inserting a probe into a body of a living subject, the probe having a tip, an ablation electrode and a plurality of microelectrodes;
    establishing a contacting relationship between two of the microelectrodes and a target tissue;
    energizing the ablation electrode at a power level; while the ablation electrode is energized, measuring impedances of the microelectrodes and determining a pair of the microelectrodes having a highest and second highest impedance for determining a bipolar impedance between the pair of the microelectrodes; and
    responsively to the bipolar impedance, adjusting the power level of the ablation electrode.

2. The method according to claim 1, further comprising the steps of:
    iteratively performing the step of measuring impedances of the microelectrodes; and
    estimating a tissue temperature from a change between a first performance and a second performance of measuring impedances.

3. The method according to claim 2, further comprising the steps of:
    making a determination that the tissue temperature exceeds a predetermined limit; and
    responsively to the determination reducing the power of the ablation electrode.

4. The method according to claim 3, wherein reducing the power comprises deactivating the ablation electrode by reducing the power to zero.

5. The method according to claim 1, wherein measuring impedances of the microelectrodes comprises polling the microelectrodes to determine pairwise impedances therebetween.

6. The method according to claim 1, wherein establishing a contacting relationship comprises determining a location and orientation of the tip of the probe with respect to the target tissue with six degrees of freedom.

7. The method according to claim 1, wherein measuring impedances of the microelectrodes comprises polling the microelectrodes to determine impedances between the microelectrodes and an indifferent electrode.

8. The method according to claim 1, wherein the probe has a lumen, further comprising the step of deploying an inflatable balloon through the lumen, the balloon having a longitudinal axis and an exterior wall, the microelectrodes being disposed circumferentially about the longitudinal axis on the exterior wall.

9. The method according to claim 8, the balloon further comprising a subassembly comprising a plurality of strips extending longitudinally on the exterior wall of the balloon, wherein the microelectrodes are disposed on the strips.

* * * * *